United States Patent [19]
Douthart et al.

[11] Patent Number: 5,707,506
[45] Date of Patent: Jan. 13, 1998

[54] CHANNEL PLATE FOR DNA SEQUENCING

[75] Inventors: Richard J. Douthart, Richland; Shannon L. Crowell, Eltopia, both of Wash.

[73] Assignee: Battelle Memorial Institute, Richland, Wash.

[21] Appl. No.: 643,820

[22] Filed: May 6, 1996

Related U.S. Application Data

[63] Continuation-in-part of Ser. No. 330,876, Oct. 28, 1994, Pat. No. 5,514,256.

[51] Int. Cl.$^6$ .......................... G01N 27/26; G01N 27/447
[52] U.S. Cl. ........................ 204/622; 204/456; 204/466; 204/606; 204/618; 204/619; 204/621
[58] Field of Search ........................ 204/606, 607, 204/608, 609, 610, 612, 613, 614, 615, 616, 617, 618, 619, 620, 621, 470, 469, 468, 467, 466, 465, 464, 463, 462, 461, 459, 458, 457, 456

[56] References Cited

U.S. PATENT DOCUMENTS

| | | | |
|---|---|---|---|
| 3,047,489 | 7/1962 | Raymond | 204/616 |
| 4,061,561 | 12/1977 | Fletcher et al. | 204/616 |
| 4,130,471 | 12/1978 | Grunbaum | 204/462 |
| 4,151,065 | 4/1979 | Kaplan et al. | 204/620 |
| 4,417,967 | 11/1983 | Ledley | 204/466 |
| 5,104,512 | 4/1992 | Gombocz et al. | 204/607 |
| 5,139,637 | 8/1992 | MacConnell | 204/466 |
| 5,192,412 | 3/1993 | Kambara et al. | 204/612 |
| 5,217,593 | 6/1993 | MacConnell | 204/457 |
| 5,399,255 | 3/1995 | Sarrine | 204/616 |

*Primary Examiner*—Kathryn L. Gorgos
*Assistant Examiner*—John S. Starsiak, Jr.
*Attorney, Agent, or Firm*—Paul W. Zimmerman

[57] ABSTRACT

This invention is a channel plate that facilitates data compaction in DNA sequencing. The channel plate has a length, a width and a thickness, and further has a plurality of channels that are parallel. Each channel has a depth partially through the thickness of the channel plate. Additionally an interface edge permits electrical communication across an interface through a buffer to a deposition membrane surface.

18 Claims, 7 Drawing Sheets

CHANNEL PLATE FOR DNA SEQUENCING

This application is a continuation-in-part of application Ser. No. 08/330,876 filed Oct. 28, 1994, U.S. Pat. No. 5,514,256.

This invention was made with Government support under Contract DE-AC06-76RLO 1830 awarded by the U.S. Department of Energy. The Government has certain rights to the invention.

FIELD OF THE INVENTION

The present invention relates specifically to a channel plate useful for electrophoretic DNA sequencing, separation and hybridization including DNA fingerprinting and restriction enzyme mapping.

BACKGROUND OF THE INVENTION

Over 40 million bases of genetic code originating from various organisms from humans to virus have been elucidated in the laboratory over the last decade. One of the objectives of the Human Genome Project is to sequence the approximately 3 billion bases that make up the human genome. Obviously, significant advances need to be made in DNA sequencing technology if this goal is ever to be achieved in a reasonable time.

The standard electrophoresis method is separation through a continuous polyacrylamide slab gel. In the preparation of a gel slab the liquid polyacrylamide gel is poured as a single continuous sheet between two glass plates separated by spacers at the boundaries. The two glass plates are smooth and flat. When the gel polymerizes a glass plate-gel-glass plate sandwich is formed. Sample loading slots are cast in the gel using a plastic comb shaped device set in place before the gel polymerizes and removed before loading the samples. Alternatively, sample loading slots may be formed with a sharks tooth comb inserted into polymerized gel. This format is limited in the degree of data compaction that can be achieved in one run due to difficulties in lateral stability (sample drift) that occurs if the sample wells are placed any closer than 0.2 mm to one another and are any smaller than 4.0 mm in width. As a consequence of this limitation, improvements in slab technology have centered around decreases in running time and increases in the degree of resolution rather than increases in data compaction. The most significant advancement in this direction is the development of ultra-thin slab gels using extremely thin spacers that increase resolution and decrease running times.

A technology that does not appear to be limited by data compaction considerations is the recent development of gel-filled capillaries. Each capillary is an isolated electrophoresis unit that accepts a single sample and is limited theoretically only by the dimensions of the capillary. The large surface to volume ratio of the capillary allows highly efficient dissipation of electro- resistant generated heat. The greater the de-coupling of gel temperature from electro-resistive generated energy the greater the effective field strength that can be applied. The linear range over which migration rate varies directly with field strength is extended using gel filled capillaries allowing separations at higher fields with greatly reduced running times.

The advantage in a single capillary, however, must somehow be translated to a large array of coupled capillaries each with the same characteristics which can be electrophoresed together under identical conditions to make this technology viable for DNA sequencing and to achieve significant data compaction. It is extremely difficult to reload gel into a capillary after the initially loaded gel is spent.

Both the gel slab and the gel-filled capillary technologies require post processing of either a direct readout, for example autoradiograph or on-the fly florescence detection through appropriate windows near the end of the electrophoresis gel, or an indirect readout requiring hybridization, for example multiplexing by elution or direct blotting, followed by a direct readout. Upon simultaneous electrophoresis, fragment bands will form of size determined by the dimensions of the gel sample wells and will migrate in the order of the DNA sequence. These fragment bands that make up the ladders can be labeled before separation with either radioactive or florescence labels. Another technique is to label each of the four types of nucleotide termination with a specific florescent molecule. Since the emission spectra of each label is different, a mixture of all four reactions can be electrophoresed from the same well in the gel effectively increasing data compaction four fold. In other techniques, for example multiplexing, the resolved bands can be elucidated by hybridizing electro-eluted fragments on deposition membranes to specific labeled DNA fragment probes.

The lower limit for width of a single slab-gel loading well on a conventional DNA sequencing apparatus is approximately 4 mm, with a required spacing between adjacent wells of about 0.2 mm. If these dimensions are decreased to increase data compaction, significant ladder drift and data cross talk occur during electrophoresis which severely limits the accuracy of the data. With these limitations only about 48 lanes can be run.

In U.S. Pat. No. 4,891,120 to Sethi et al., there is described a semiconductor having one or more longitudinal channels. It is mentioned that DNA sequencing and probe analysis may be done using the channelled semiconductor. However, a semiconductor is limited to low voltages for electrophoresis to avoid overheating a DNA sample. Moreover, the channel lengths are limited in length to the size of a semi-conductor chip thereby limiting DNA sequencing resolution. Therefore, standard electrophoresis equipment cannot be used because the standard electrophoresis equipment requires much larger plates.

SUMMARY OF THE INVENTION

The present invention is a channel plate made of an electrically non-conductive non-cellulosic material which provides increased productivity in terms of data density packed into a single run with concomitant increases in sequencing speed and data resolution. The channel plate consists of a plate with a series of adjacent micro channels which can replace the conventional slab gel and is useable in standard electrophoresis equipment, for example DNA sequencing machines made by Applied Biosystems, Inc., Beckman Instruments, and Pharmacia. When cast with gel, each micro-channel represents an electrophoresis lane isolated and independent of its neighbors which eliminates the common problem of drift and interference that limits data compaction of standard continuous slab gels when loading density is increased.

Other aspects of the device enables efficient processing in the identification of DNA sequences by any one of the available detection methods including multiplex sequencing. Still another aspect is an increase of speed in DNA sequencing because of the ability to run at higher electric fields with efficient temperature control of the channel plate.

The invention herein described, under optimal conditions can process about 24,000 (48 reaction sets (with each reaction set occupying 4 lanes),×500 bases per sequence length) bases per run. The adaptation to multiplexing increases the output by about another factor of 40 per run to 96,000 data points. This estimation is based upon the number of distinct multi-plexing (40) vectors reported by Church. The throughput estimation is nearly the million or so bases per run needed for efficient completion of the Human Genome Project in a reasonable time frame.

DESCRIPTION OF THE PREFERRED EMBODIMENTS

Figures 1A, 1B:
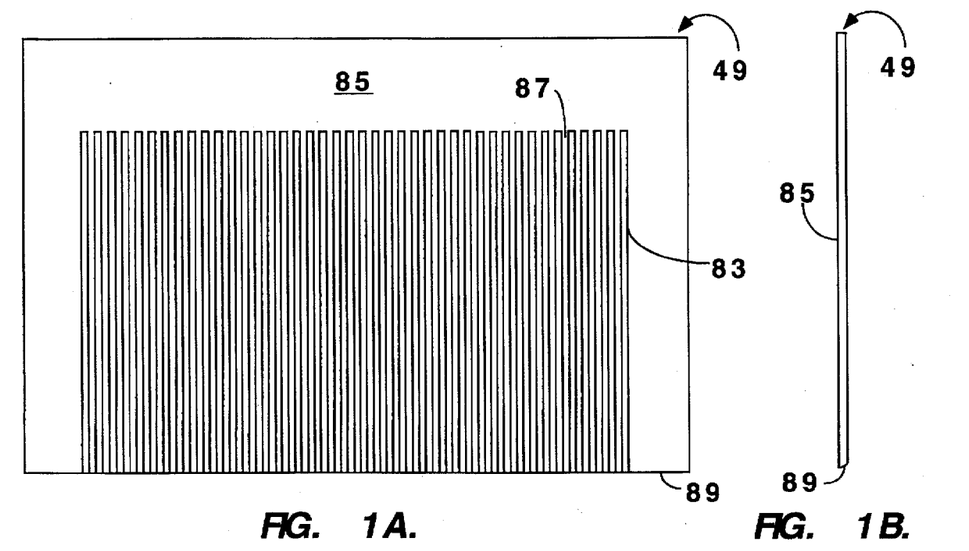
FIG. 1a Is a top view of the horizontal channel plate.
FIG. 1b Is a side view of the horizontal channel plate.

The present invention is a non-electrically conductive non-cellulosic channel plate shown in FIG. 1a and FIG. 1b.

The channel plate 49 in FIG. 1a is not to drawn scale for the sake of clarity, showing much fewer than the present 192 individual channels 83. The channels 83 can be etched, machined or cast in glass, ceramic, plastic or other electrically non-conductive, non-cellulosic material compatible with polyacrylamide or other suitable gel. The preferred material for the channel plate 49 is the ceramic Macor™ manufactured by Corning Glassware which is machinable to close tolerances and is compatible with polyacrylamide gel. Glass or plastic may also be used.

Figure 1C:
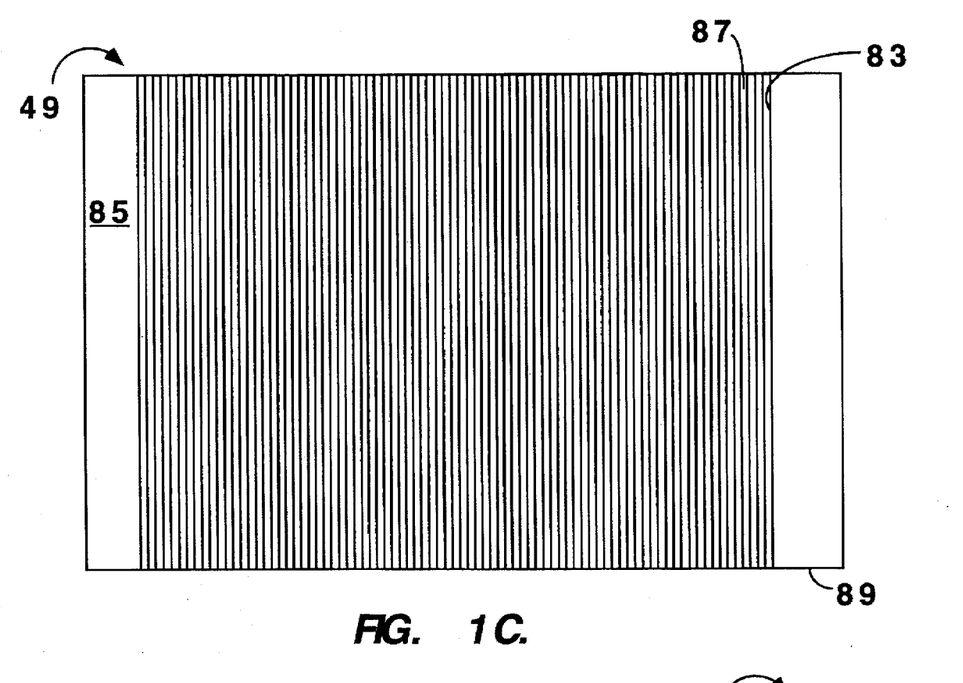
FIG. 1c is a top view of the vertical channel plate.

The individual channels 83 of channel plate 49 are filled with the gel. DNA samples may be introduced into each channel 83 containing gel with a syringe, (not shown). Hence, the width of a channel 83 and the spacing between channels 83 is primarily limited by the minimum size syringe and the dielectric constant of the channel plate material respectively. FIG.1a and 1b show a channel plate 49 for use in a horizontal orientation. For a vertical orientation, it is preferred that the channels 83 extent across the full width of the channel plate 49 as shown in FIG. 1c.

Figures 2A, 2B:
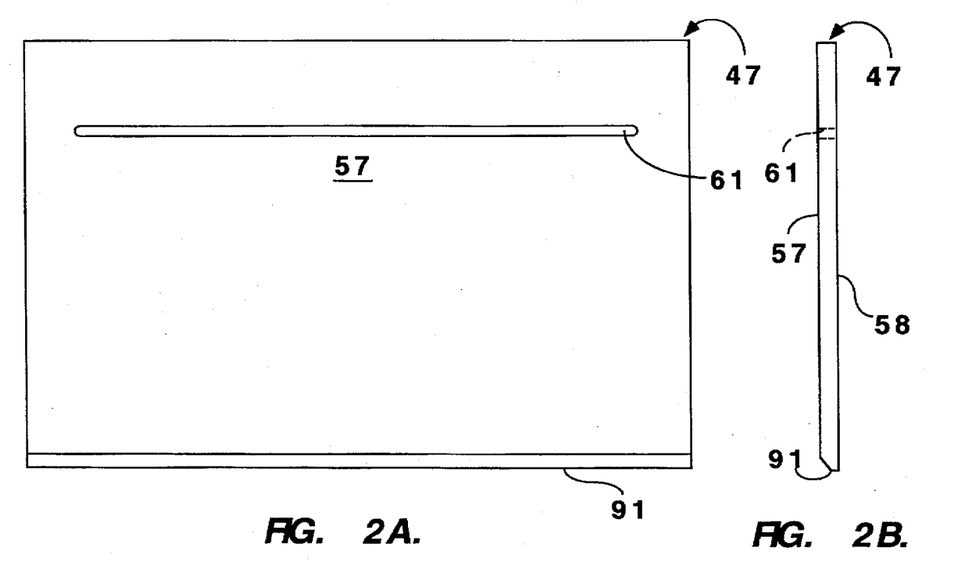
FIG. 2a Is a top view of the horizontal cover plate.
FIG. 2b Is a side view of the horizontal cover plate.
Figure 2C:
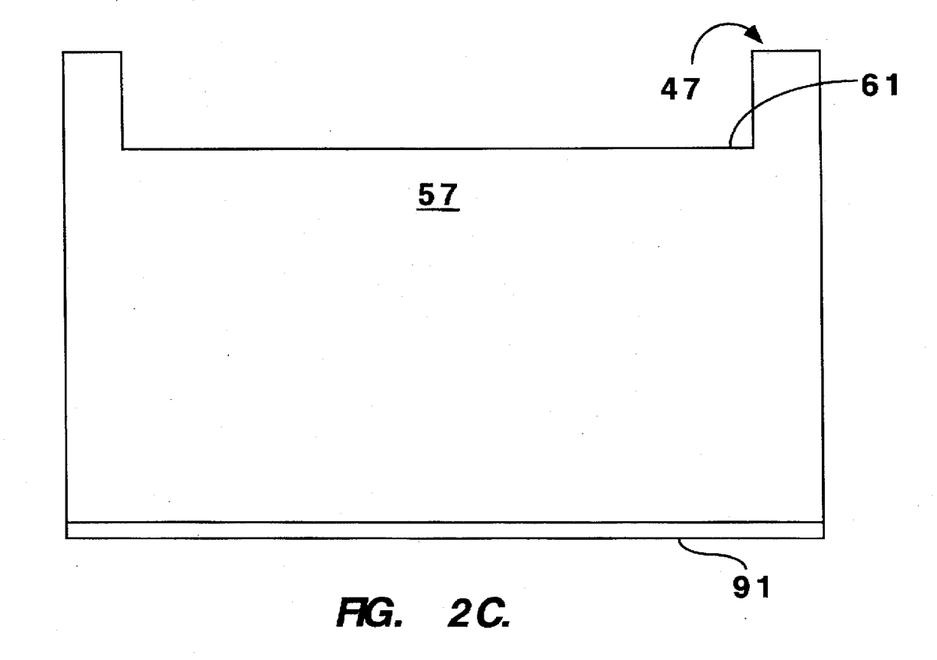
FIG. 2c is a top view of the vertical cover plate.

It is preferred to combine the channel plate 49 with a cover plate 47 (FIG. 2a, FIG. 2b) to contain the gel. When combined, the upper surface 85 of the channel plate 49 and the underside (not shown) of the cover plate 47 need to be faced or polished to a true flatness. When fitted together they should prevent liquid from flowing between the channel walls 87 that separate the individual channels 83 after the gel has polymerized. A thin treated polyester gasket (not shown) can be used if needed between the channel plate 49 and the cover plate 47. The preferred material of the cover plate 47 is Pyrex™ glass. Both the cover plate 47 and the channel plate 49 should be worked together as a unit when polishing and making the bottom edges flat, to assure complete trueness. The cover plate 47 with narrow slot 61 (FIG. 2a) is used in a horizontal orientation of the channel plate 49. For vertical orientation, the cover plate is modified to have a wide slot 61 (FIG. 2c).

Optionally, the edges 89, 91 may be bevelled for adaptation to direct deposition electrophoretic devices.

Channel Plate Material

The selection of channel plate material is critical to the present invention. It is necessary that the channel plate material be electrically non-conductive so that electric current is only conducted by the gel. Also, the material must not absorb the gel or the DNA sample. Hence, wood, paper and other cellulosic materials are not suitable.

Glass is of particular interest because of its low cost, availability, and transparency. While glass is useful, the gel does not easily wet the glass surface. In addition, glass is difficult to machine. Hence, channel plates made from glass may preferably be cast or etched rather than machined.

Plastic is also available and inexpensive.

During our experiments, we decided to try a machinable glass ceramic which, unexpectedly, resulted in excellent performance because the gel wet the surface of the machinable glass ceramic. Even though the specific material cost is higher for machinable glass ceramic, it is preferred because a wettable channel plate may be constructed with standard machining.

Figure 3A:
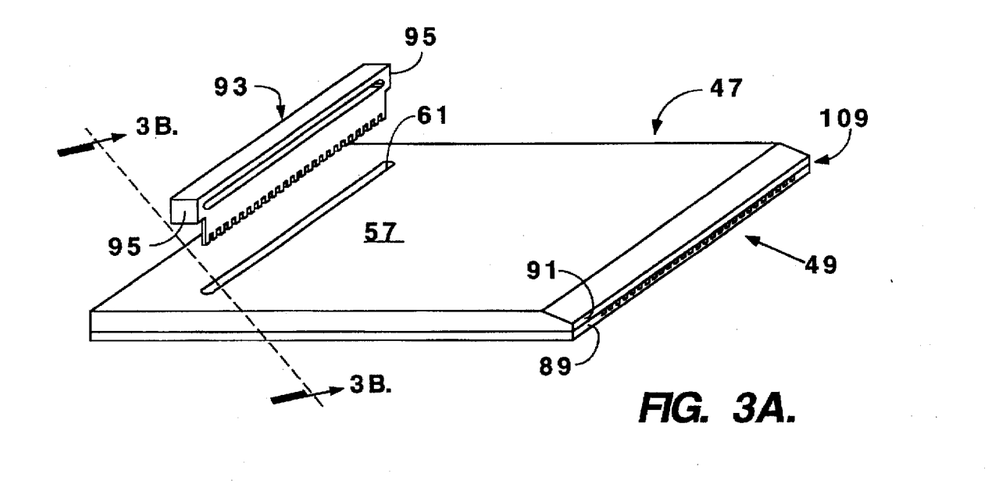
FIG. 3a Is a isometric view of the horizontal plate assembly with the gel displacement comb positioned for insertion.
Figure 3B:
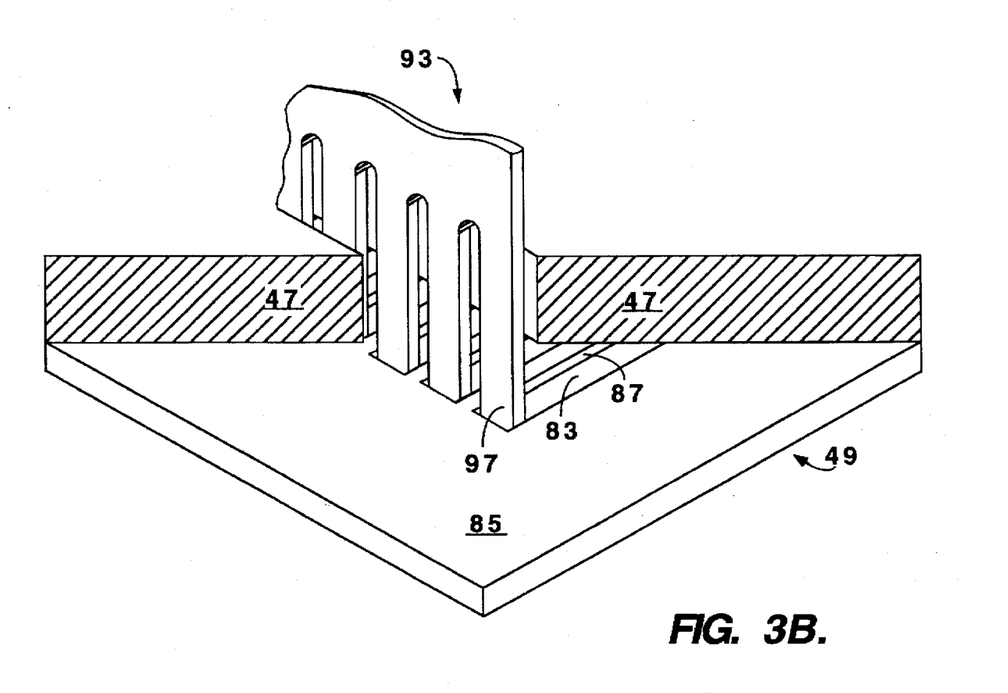
FIG. 3b is a cross-sectional view of the horizontal plate assembly along line 3b—3b illustrating the gel displacement comb in the inserted position.
Figure 3C:
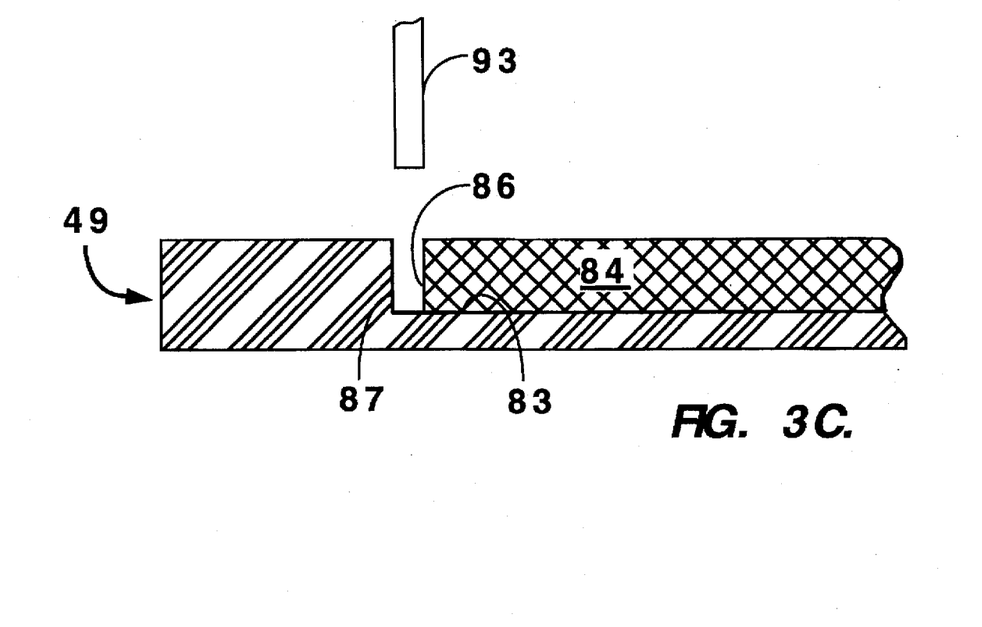
FIG. 3c A cross-sectional view of the horizontal channel plate illustrating a receiving well.
Figure 3D:
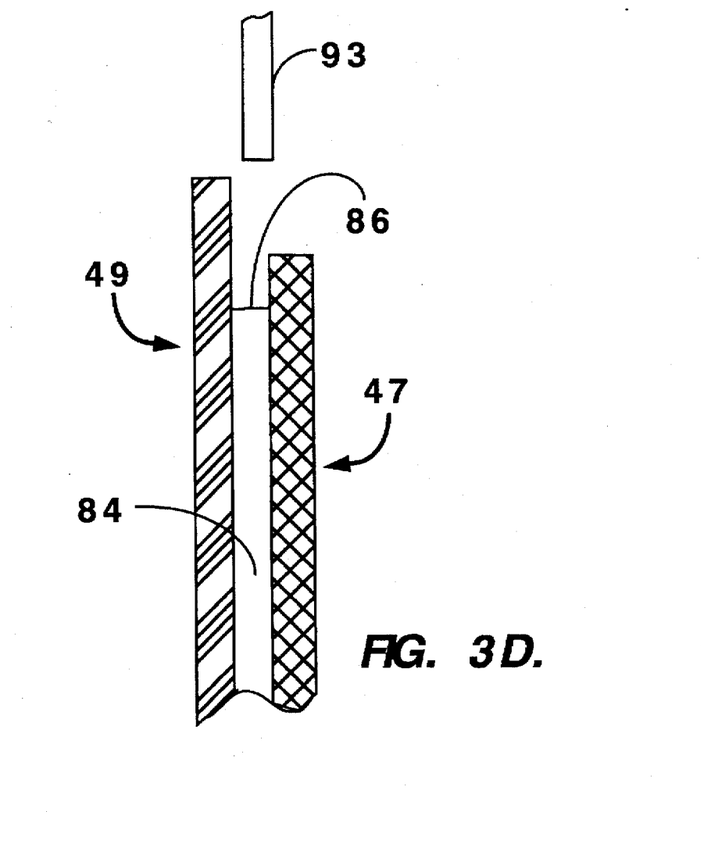
FIG. 3d A cross-sectional view of the vertical channel plate illustrating a receiving well.

FIG. 3a, FIG. 3b, FIG, 3c, and FIG. 3d illustrate the use of a gel displacement comb 95 for making sample receiving wells 86 for both horizontal and vertical orientations of the channel plate 49. The individual comb teeth 97 fit snugly into each channel 83, blocking gel from a small upper portion of the channel, thus reserving a space for sample loading. FIG. 3b shows a close up cross section view of the comb teeth 97 inserted into the channels 83. Again the dimensions in FIG. 3a, FIG. 3b and FIG. 3c are exaggerated for clarity.

Once the gel has polymerized in the channels 83 the gel displacement comb 93 is removed leaving sample receiving wells 86 as illustrated in FIG. 3c. The specific type of sample loading device for placing a DNA sample into the receiving wells 86 is not critical to the practice of the instant invention. However, placing samples is preferably accomplished with individual or ganged fine gauge glass barrel syringes (not shown).

Figure 5:
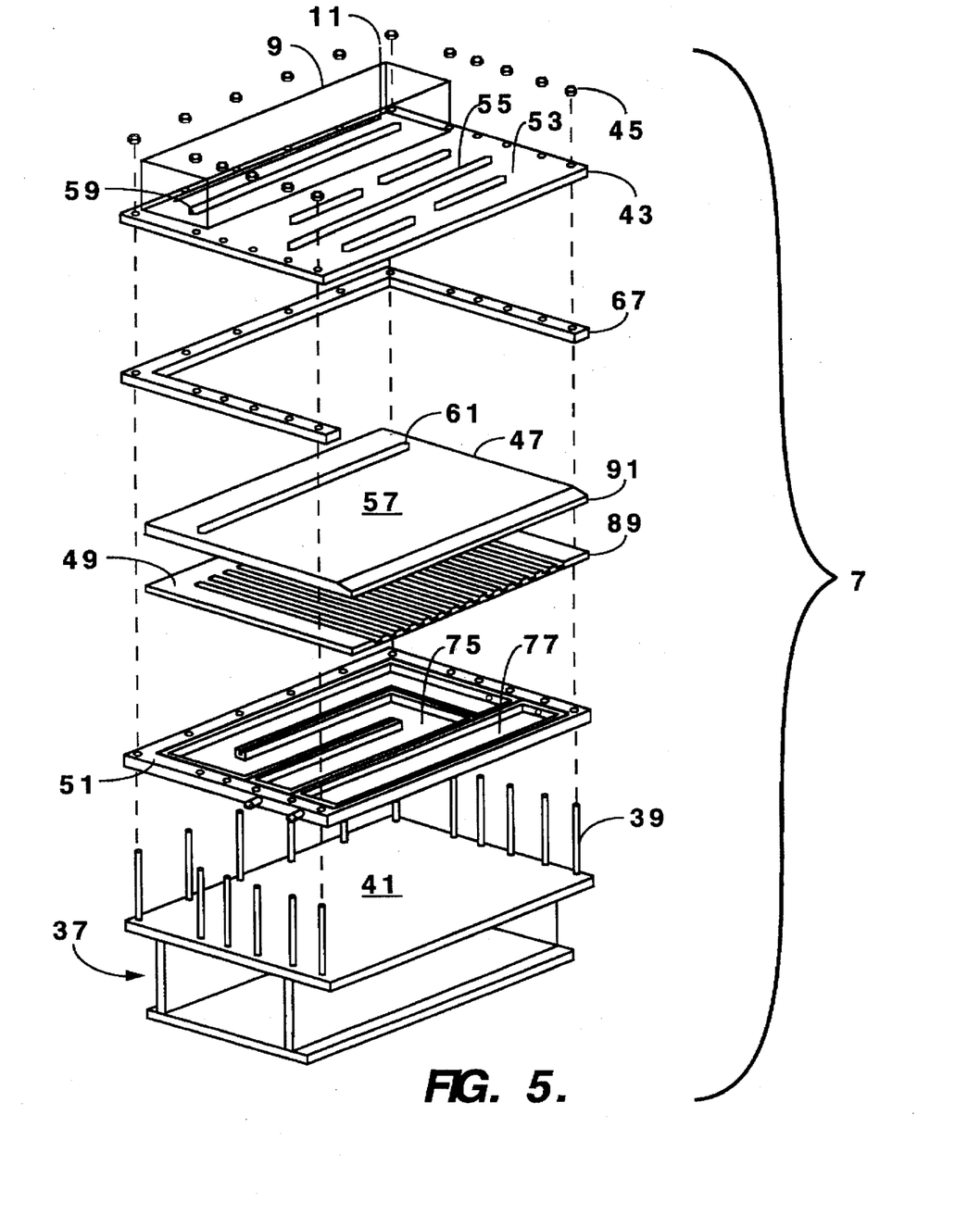
FIG. 5 Is an isometric representation of an expanded view of the components of the gel support unit.

Insertion of the gel displacement comb 93 into the horizontal plate assembly 7 illustrated in FIG. 5, requires the gel displacement comb 93 to be inserted through the access slot 61 in the cover plate 47 such that the individual comb teeth 97 protrude into the bottom of each channel 83 as illustrated in FIG. 3b. The gel displacement comb 93 is snug fitting within the channels 83 and the access slot 61 cut through the cover plate 47. The gel displacement comb 93 is treated with a siliconizer spray prior insertion to ensure easy withdrawal without pulling out clinging fragments of gel. The gel displacement comb 93 is rigidly snapped into position prior to the polymerization of the liquid gel. Tabs 95 may be provided on each end of the gel displacement comb 93 to slide into recesses in each end of an upper buffer chamber (not shown).

The comparatively rugged isolation of each channel's loading well from its neighboring loading well and the "snap in fit" allows the design of an albeit miniature but rugged ganged loading manifold (not shown).

Utilization of a Vertical Embodiment

Although FIGS. 3a, 3b and 3c depict a horizontal orientation of the channel plate 49, it will be recognized by those of skill in the art of DNA electrophoresis that the electrophoresis is insensitive to channel plate orientation insofar that the DNA sample is retained in the receiving wells 86. If it is desired to orient the channel plate 49 vertically prior to sample loading, then the construction show in FIG. 3a may be modified as shown in FIG. 3d. The narrow access slot 61 (FIG. 2a) in the cover plate 47, as well as the comb 95 would not be needed. Alternatively, DNA samples may be introduced with a syringe directly into gel in the channels 83. This substantially limits the dimensionality of the channels of the vertical channel plate 49 whose depth are strongly determined by the dimensionality of the loading device and gel displacement comb 93, if used, which must fit physically within the channels 83, entering from a vertical aspect rather than the horizontal aspect of the preferred embodiment.

Heat Transfer From Channel Plate During Electrophoresis

After the sample is loaded, the channel plate 47 is subjected to electrical energy having from about 30 V/cm to about 500 V/cm. This electrical energy is spent in causing the DNA sample to migrate through the gel. It is necessary that the channel plate 47 be maintained at a constant temperature.

Figure 4A:
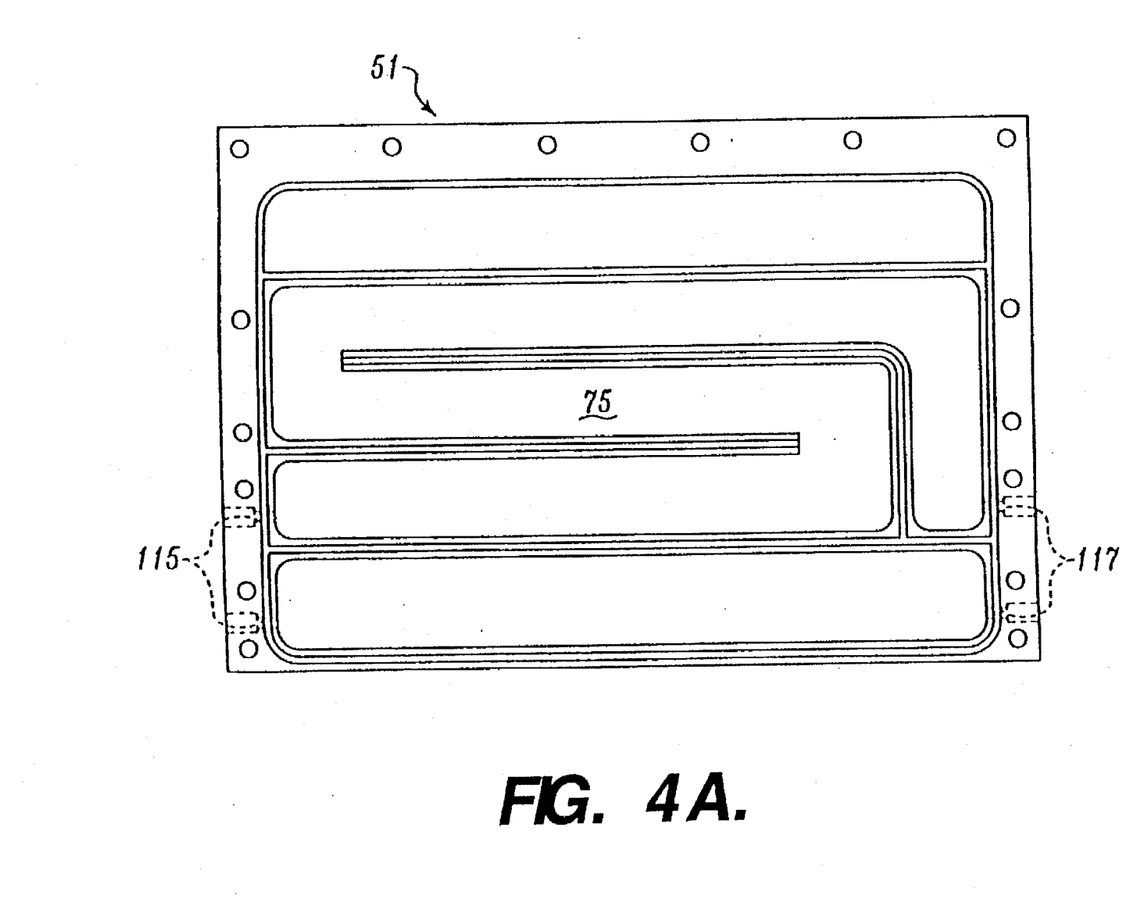
FIG. 4a Is a top view of the temperature control plate.
Figure 4B:
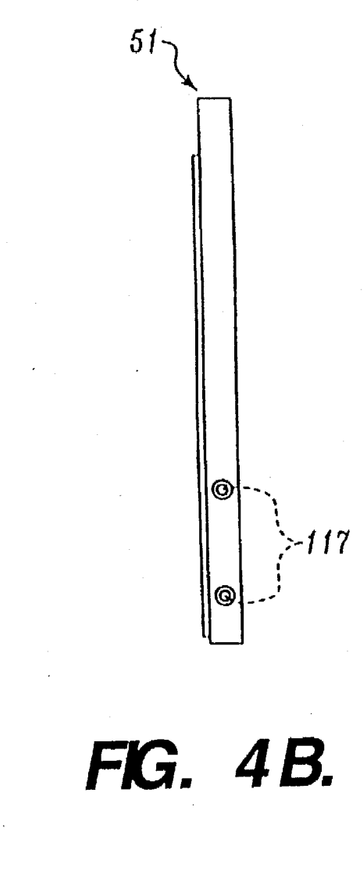
FIG. 4b Is a side view of the temperature control plate.

Accordingly, it is preferred that the lower surface (not shown) of the channel plate 47 have a surface area permitting natural convection/dissipation of heat at a rate substantially equal to or greater than the rate of electrical heat generation. In situations where the electrical heat generation exceeds the rate of natural convection/dissipation from the lower surface, a temperature control plate 51 may be placed on the lower surface of the channel plate 49 (FIG. 4).

The temperature control plate 51, through which a temperature controlling liquid can be circulated is sealed to the back of the channel plate 49 using recessed neoprene gaskets 81. The temperature of the plate assembly 7 can be controlled by circulating a temperature controlled fluid through the chamber 75 via inlet port(s) 115 and outlet port(s) 117. This allows the bulk of the plate assembly 7 to be run at elevated temperatures of 40°–60° C.

Plate Assembly

FIG. 5 is an illustration of an expanded parts breakdown of a plate assembly 7. The channel plate 49 may be filled with gel and subjected to electrophoresis support table 37. The system is held together by threaded studs 39 evenly dispersed and countersunk into the upper platform 41 of the support table 37. It is preferred that the threaded studs 39 are not electrically conductive. Accordingly, plastic threaded studs 39 are preferred. The pressure plate 43 is secured by hex head nuts 45 to the threaded studs 39 of the support table 37. Sandwiched between the pressure plate 43 and the temperature control plate 51 are the cover plate 47, and the channel plate 49. The pressure plate 43 is continuous with the upper buffer chamber 9 which contains the upper electrode 11.

Figure 6A:
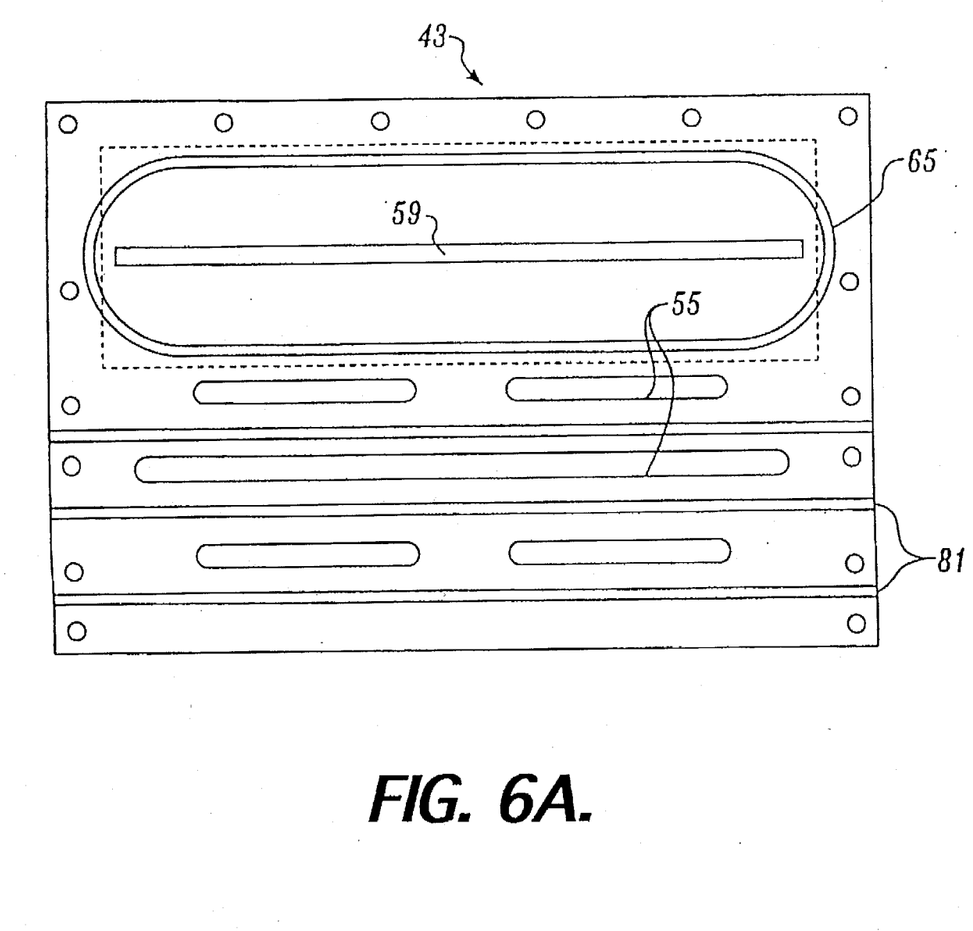
FIG. 6a Is a top view of the pressure plate.
Figure 6B:
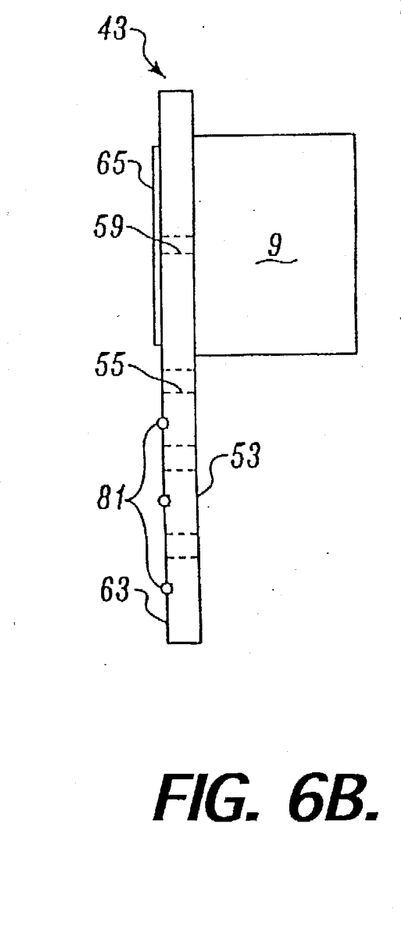
FIG. 6b Is a side view of the pressure plate.

The upper surface 53 of the pressure plate 43 has a multiplicity of horizontal slits 55 which allow access to the upper surface 57 of the cover plate 47 for temperature monitoring during a sequencing run. The lower surface 58 of the cover plate 47 fits against the upper surface of the channel plate 49. The bottom surface of the pressure plate 63 illustrated in FIG. 6a, FIG. 6b has recessed channels with a neoprene O-ring gasket 65 that leak seals the upper buffer chamber 9 around the access slot 61 in the cover plate 47.

Referring again to FIG. 5, the U-shaped spacer bar 67 serves to align the channel plate 49 to the cover plate 47.

Pouring the Gel

The plate assembly 7 is assembled into a unit as illustrated in FIG. 5. Liquid gel is poured into the plate assembly 7 through the access slot 61 in the cover plate 47 from the access slot 59 in the bottom of the upper buffer chamber 9. The protruding interface edge 109 of the plate assembly 7 is wrapped in a loosely fitting Parafilm bag which catches excess liquid gel. Once the gel has polymerized, the excess protruding gel will be cut flush with the interface edge 109 using a sharp razor blade. It is imperative that the cover plate 47 and the channel plate 49 be in perfect alignment at the interface edge 109. This is accomplished by aligning the cover plate 47 and the channel plate 49 with a straight edge (not shown) before the hex head nuts 45 of the plate assembly 7 unit are completely tightened. The U-shaped spacer bar 67 will also help to align the channel plate 49 to the cover plate 47.

The gel displacement comb 93 is snapped into place (FIG. 3b) before the gel polymerizes and carefully removed (FIG. 3c) after the gel sets.

Construction of the Unit Components

Referring again to FIG. 3a of the gel support unit that consists of the channel plate 49, and the cover plate 47. The channel plate 49 illustrated in FIG. 1a can be machined with various channel depths and widths with great control over the channel 83 dimensions. Typically the depth<0.2 mm is less than the width<0.4 mm to preserve some band like quality to the resolved fragments. These channel dimensions are limited only by fabrication limits and loading considerations of the small sample size, and not by intrinsic factors such as data degeneration due to lane drift and cross talk that limit thin slab gels.

If the plate assembly 7 is to be used without a gasket, the glass cover plate 47 should be ground to a true flatness. The inside surface of the access slot 61 should be polished to insure easy insertion and removal of the gel displacement comb 93 and sample loading devices (not shown). The polishing will also help prevent cracking of the cover plate 47 across the access slot 61 which can occur due to uneven pressure applied by the upper pressure plate 43 illustrated in FIG. 5 or by extreme temperature variations during the electrophoresis run if temperature control is inadvertently lost.

Use of Gasket Material

Referring to FIG. 5 the physical and electrical isolation of one channel from another can sometimes be aided by a thin transparent polyester gasket (not shown) placed between the channel plate 49 and the cover plate 47. The gasket is useful when using glass cover plates 47 with an uneven bottom surface and with channel plates 49 where slight irregularities along the upper surfaces of the channel walls 87 exist.

However, it should be noted that experiments have indicated the functioning of the channel plate 49 is not dependent on using a gasket. Actually, successful DNA sequencing and assemblage of the plate assembly 7 is much simpler when a gasket is not used. Transparent 0.1 mm thick polyester sheets are a suitable gasket to obtain seals between the channel plate 49 and the glass cover plate 47. Gaskets that are highly deformable are not desired here since under slight pressure, the excess gasket material will compete with gel in the channels 83. The polyester gaskets should be treated with a 6N KOH and then silated with Trimethoxysilylpropyl-methacrylate.

OTHER USES OF THE INSTANT INVENTION

The components of this invention, either as an integrated entity or individually, can be used productively for other applications besides DNA sequencing. For example, DNA fingerprinting with specific probes could be accomplished with increased throughput and resolution, and decreased electrophoresis time using a channel plate.

Example 1

Several experiments were done to demonstrate the use of plastic as a channel plate. Lexan was the plastic used. Upon applying electrical voltage to the Lexan channel plate, the gel within the capillaries extruded from the channels. The Lexan channel plate was silated but no improvement was observed. In addition, it was observed that after filling the channels with gel, and the cover plate was removed, prior to electrophoresis air bubbles were present in the gel filled channels. Air bubbles were undesirable because they interfered with the electrophoresis results. However, the gel was not degassed.

Example 2

An experiment was conducted to demonstrate electrophoresis of a DNA sample using a glass ceramic channel plate. The channel plate 49 was made from a 12 inch×12 inch×1/16 inch glass ceramic (Macor obtained from San Jose Delta, Inc., Santa Clara, Calif.) and cut to a length of 32.4 cm, width of 28.6 cm and thickness of 1.5 mm. The channels 83 were 1.0 mm wide by 0.5 mm deep with a 2.0 mm center to center spacing. The channel plate 49 had 144 channels over a 28.6 cm span.

The cover plate 47 was made from Pyrex glass 1/4 inch thick and outside dimensions substantially matching the channel plate 49. The access slot 61 was 20.6 cm long and 3.2 mm wide. The underside of the cover plate 47 was faced to remove irregularities. Plates sides and mating surfaces were trued and polished simultaneously.

The temperature control plate 51 was sealed to the back of the channel plate 49 with recessed silicone sponge 3/16 inch O-ring gaskets. Temperature control was accomplished with a constant temperature bath (Haake Fe #66804). The surface temperature of the cover plate 47 was monitored with j-type thermocouples. The channel plate was maintained at about 50° C. with a thermostatted Haake pump.

Prior to assembly, both plates were cleaned with detergent and rinsed with deionized water. The plates were then dipped into 9 vol% ethanolic KOH (avoid prolonged contact of plates with KOH) the rinsed to remove any oils or grease. The plates were further rinsed with deionized water, ethanol, and finally acetone in advance of assembly. A clean residue free optical air spray (Vari-Air Plus, Janesville, Wis.) was used to dry the surfaces and remove dust.

An 8% polyacrylamide gel was made using standard procedures as may be found in Sanger, F., Nicklen. S., Coulson, A. R., "Proc. Natl. Aead. Sci." 1977, 74, 5463–5467. The gel was loaded into the channels through the access slot with a small syringe. The plate assembly was shimmed so that it was at an angle with respect to the horizontal to exploit gravity flow of gel. Gel was permitted to flow from the interface edge so that the channels were completely filled. Filling all of the channels required about 75 minutes. In several runs, the cover plate was removed to inspect the gel filled channels. In most runs, there were no air bubbles. In a couple of runs, one or a few small air bubbles were noticed in one or a few of the channels. By degassing the gel, no further air bubbles were observed. Accordingly, the gel was filtered and degassed before adding accelerator.

After removal of the comb, the sample wells were cleaned and filled with deionized water. DNA samples were placed into the deionized water in the sample wells.

Sanger (referenced above) DNA sequencing chemistries were done using the reagents and protocols provided with the US Biochemical 2.0 Sequenase kit. As a test sequence, the M13mp18 vector without insert was sequenced using the primer supplied with the kit.

Electrophoresis was at 45 V/cm over 54 minutes. No extrusion of the gel was observed from the glass ceramic (Macor) channels.

Subsequent handling and processing of the deposition surface resulted in an autoradiograph having over 7000 data points which is surprisingly greater than the 1875 data points expected from conventional electrophoresis with a single fluorophor label per lane. The individual lanes were straight with minimal drift. Some of the lanes showed poor results. Upon examination, it was found that these lanes were contaminated with air bubbles. Again, after using the degassing step, no further air bubbles were observed with the ceramic channel plate.

OTHER EMBODIMENTS

While a preferred embodiment of the instant invention has been illustrated and described, it will be apparent to those skilled in the art that many changes and modifications may be made without departing from the invention in its broader aspects. The appended claims are therefore intended to cover such changes and modifications as fall within the true spirit and scope of the invention.

We claim:

1. A channel plate for electrophoresis sequencing of a DNA sample, said channel plate having (a) a length, a width and a thickness, and further having, (b) a plurality of channels that are parallel placed upon an upper surface of the channel plate, each channel having a depth partially through the thickness and filled with a gel, wherein the improvement comprises:

(c) said channel plate is made from electrically non-conductive, non-cellulosic material, and (d) a temperature control plate attached to a lower surface wherein a temperature of the channel plate is controlled.

2. The channel plate as recited in claim 1, wherein said temperature control plate contains at least one baffle chamber.

3. The channel plate in claim 1, wherein the channel plate is vertically oriented.

4. The channel plate as recited in claim 1, wherein the channel plate is horizontally oriented.

5. The channel plate as recited in claim 1, wherein said electrically non-conductive, non-cellulosic material is a glass ceramic.

6. The channel plate as recited in claim 5, wherein said glass ceramic is a machinable glass ceramic.

7. A method of preparing a DNA sample for electrophoretic separation, comprising the steps of:
   (a) providing a glass ceramic channel plate having a length, width and thickness, further having a plurality of parallel channels formed partially through the thickness and each channel having a first end at a position distant from a first edge, each of the channels extending therefrom to an interface edge;
   (b) filling the channels with a gel;
   (c) placing a cover plate over the channels thereby covering the channels and confining the gel within the channels;
   (d) inserting a comb into the channels;
   (e) permitting the gel to polymerize with the comb in place;
   (f) withdrawing the comb after polymerization of the gel and leaving, sample wells; and
   (g) filling the sample wells with DNA sample.

8. The method as recited in claim 7, wherein said comb is inserted at the first end of the channels.

9. The method as recited in claim 7, wherein said comb is inserted at a top edge.

10. The method as recited in claim 7, further comprising the step of:
    degassing the gel prior to filling the channels.

11. The method as recited in claim 7, further comprising attaching a temperature control plate to a lower surface of said channel plate and controlling a temperature of said channel plate.

12. A channel plate for electrophoresis sequencing of a DNA sample, said channel plate having (a) a length, a width and a thickness, and further having, (b) a plurality of channels that are parallel placed upon an upper surface of the channel plate, each channel having a depth partially through the thickness and filled with a gel, wherein the improvement comprises:
    (c) said channel plate is made from a glass ceramic.

13. The channel plate in claim 12, further comprising a cover plate for containing the gel.

14. The channel plate as recited in claim 13 wherein said cover plate is made from glass.

15. The channel plate as recited in claim 13, further comprising a temperature control plate attached to a lower surface wherein a temperature of the channel plate is controlled by a fluid flow through the temperature control plate.

16. A method of preparing a DNA sample for electrophoretic separation, comprising the steps of:
    (a) providing an electrically non-conducting, non-cellulosic channel plate having a length, width and thickness, further having a plurality of parallel channels formed partially through the thickness and each channel having a first end at a position distant from a first edge, each of the channels extending therefrom to an interface edge;
    (b) filling the channels with a gel;
    (c) placing a cover plate over the channels thereby covering the channels and confining the gel within the channels;
    (d) inserting a comb into the channels;
    (e) permitting the gel to polymerize with the comb in place;
    (f) withdrawing the comb after polymerization of the gel and leaving the sample wells;
    (g) filling the sample wells with DNA sample; and
    (h) attaching a temperature control plate to a lower surface of said channel plate for controlling a temperature of said channel plate during the electrophoretic separation.

17. The method as recited in claim 16, wherein said non-electrically conducting, non-cellulosic channel plate is glass ceramic.

18. The method as recited in claim 17, wherein said glass ceramic is machinable glass ceramic.

* * * * *